(12) United States Patent
Husson et al.

(10) Patent No.: US 9,033,159 B1
(45) Date of Patent: May 19, 2015

(54) MEMBRANE SURFACE MODIFICATION

(75) Inventors: Scott M. Husson, Greenville, SC (US);
Bharat V. Bhut, Jamesville, MN (US)

(73) Assignee: Clemson University, Clemson, SC (US)

( * ) Notice: Subject to any disclaimer, the term of this patent is extended or adjusted under 35 U.S.C. 154(b) by 423 days.

(21) Appl. No.: 13/489,961

(22) Filed: Jun. 6, 2012

Related U.S. Application Data

(60) Provisional application No. 61/494,182, filed on Jun. 7, 2011.

(51) Int. Cl.

| | |
|---|---|
| B01D 39/00 | (2006.01) |
| B01D 39/14 | (2006.01) |
| B01D 67/00 | (2006.01) |
| B01D 71/06 | (2006.01) |
| B01D 71/10 | (2006.01) |
| B29C 44/04 | (2006.01) |
| B01D 71/34 | (2006.01) |
| B01D 71/82 | (2006.01) |

(52) U.S. Cl.
CPC ............... *B01D 71/34* (2013.01); *B01D 71/82* (2013.01)

(58) Field of Classification Search
CPC ............... B01D 39/00; B01D 39/0067; B01D 67/0093; B01D 2323/38; B01D 69/02; B01D 71/34; B01D 67/0018; B01D 71/68; B01D 71/78; B01D 71/26; B01D 15/361; B01D 71/12
USPC ................. 210/500.34, 500.35, 500.43, 490, 210/500.29, 500.36, 500.27, 500.41; 264/41, 48; 427/244; 527/21
See application file for complete search history.

(56) References Cited

U.S. PATENT DOCUMENTS

| | | | |
|---|---|---|---|
| 7,049,373 | B2 | 5/2006 | Matyjaszewski et al. |
| 7,368,564 | B2 * | 5/2008 | Whiteford et al. ............ 540/145 |
| 7,868,087 | B2 * | 1/2011 | Mayes et al. ................. 525/54.1 |
| 8,182,695 | B2 * | 5/2012 | Whiteford et al. ............ 210/654 |
| 8,822,610 | B2 * | 9/2014 | Jakubowski et al. ........... 526/90 |
| 2007/0251883 | A1 * | 11/2007 | Niu .............................. 210/653 |
| 2008/0081999 | A1 * | 4/2008 | Gravely et al. ................ 600/473 |
| 2008/0139689 | A1 * | 6/2008 | Huang et al. ................... 522/67 |
| 2009/0176951 | A1 * | 7/2009 | Matyjaszewski et al. .... 526/200 |
| 2014/0024776 | A1 * | 1/2014 | Charles et al. ............... 525/54.1 |
| 2014/0072956 | A1 * | 3/2014 | Lu et al. ............................ 435/5 |

* cited by examiner

*Primary Examiner* — Ana Fortuna
(74) *Attorney, Agent, or Firm* — Dority & Manning, P.A.

(57) ABSTRACT

Processes for preparation of macroporous membranes having unusually high equilibrium protein binding capacities are described. Membranes include a self-supporting porous membrane substrate and a grafted polymeric film on the pore surfaces of the substrate. A polymeric film may be grafted to the porous membrane substrate using surface-initiated polymerization. The grafted polymer chains within the polymeric film can act as molecular 'brushes' or 'tentacles' in solution and can contain one or more capture chemistries for biomolecules. Membranes can be used in the separation and purification of biomolecules such as proteins, nucleic acids, virus or virus-like particles, endotoxins, and the like.

26 Claims, 3 Drawing Sheets

MEMBRANE SURFACE MODIFICATION

CROSS REFERENCE TO RELATED APPLICATIONS

This application claims filing benefit of previously filed U.S. Provisional Patent Application Ser. No. 61/494,182 having a filing date of Jun. 7, 2012, incorporated herein by reference in its entirety.

BACKGROUND

Ion-exchange chromatography is a very widely used unit operation in the biopharmaceutical industry for the downstream processing of protein therapeutics at capture, intermediate, and polishing purification stages. Ion exchange agents contain charged functional groups attached to a solid base matrix. The functional groups can be charged positively (anion-exchangers) or negatively (cation-exchangers) and interact with charged molecules primarily via electrostatic interactions. Historically, resin-based chromatography has been a work horse for the industry. While effective and reliable, this unit operation has low mass throughput, high pressure drop and complex scale-up criteria. These limitations, combined with tremendous pressure from global competition and government regulations, are forcing the biopharmaceutical industry to look for an alternative to resin column chromatography.

In recent years, membrane chromatography has been promoted as a promising alternative to conventional resin chromatography. Membrane chromatography was introduced several years ago as a technology especially suited for large-scale processes—an unmet need of biotechnology and biopharmaceutical industries. Traditionally, adsorptive ion-exchange membranes have been produced using physical polymer coating techniques such as dip coating, spray coating, meniscus coating and the like. In these techniques, the porous membrane substrate is wetted by a polymer or copolymer solution. The polymer or copolymer solution may additionally contain cross-linkers and/or other additives. The polymer coating is fixed on the membrane substrate by curing the membrane at high temperature or by a phase inversion process to produce a polymer film-coated composite membrane.

There are several disadvantages of this traditional technology. For instance, it requires multiple steps that may include polymer synthesis, coating, curing and surface functionalization of the coating material. Controlling the thickness of the polymer film coating is labor intensive and often requires the optimization of a large set of process parameters to achieve the desired thickness. Additionally, controlling the final pore size and pore-size distribution across the polymer film coated membrane produced using the phase inversion method is complex and often results in small size pores. This leads to high mass transfer resistances and limited accessibility of biomolecules within the coated membrane pores. Finally, these processes are unable to provide independent control over film thickness and polymer chain density on the surface.

Graft polymerization is a versatile technique that has been used to modify porous substrates with polymer films. However, while graft polymerization can produce a large number of binding sites on a membrane, improved control schemes are needed to avoid pore blocking and associated diffusion limited transport of biomolecules.

Previously known methods have utilized atom transfer radical polymerization (ATRP) methods for forming modified membranes. ATRP is a redox-initiated polymerization reaction in which the reaction occurs between an initiator with a radically transferable atom and a catalyst complex comprising a transition metal in a lower oxidation state that is coordinated to a ligand. Unfortunately, however, the transition metal complex in a lower oxidation state is susceptible to reaction with oxygen or other oxidizers, and promoting the metal to a higher oxidation state that serves as a deactivator for the ATRP process. Accordingly, to prepare surface modified membranes with consistent performance properties according to an ATRP process, the preformed catalysts must be stored under an inert atmosphere and experimental precautions are needed to maintain an oxygen-free environment throughout the process. Dissolved oxygen is the primary oxidizer in the surface modification formulation (mixture of monomer, catalyst complex, and solvent), and it must be removed from the solution prior to the polymerization reaction. The preparation of catalyst also must be done in a deoxygenated solvent and under an oxygen-free environment to avoid the oxidation of catalyst. Accordingly, the process of catalyst complex handling can be challenging and may become impractical at the industrial scale.

What are needed in the art are membrane preparation techniques that can yield membranes with a high polymer chain density and easily accessible protein binding sites, for instance in formation of efficient chromatographic separation materials and methods.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

DETAILED DESCRIPTION

Figure 1:
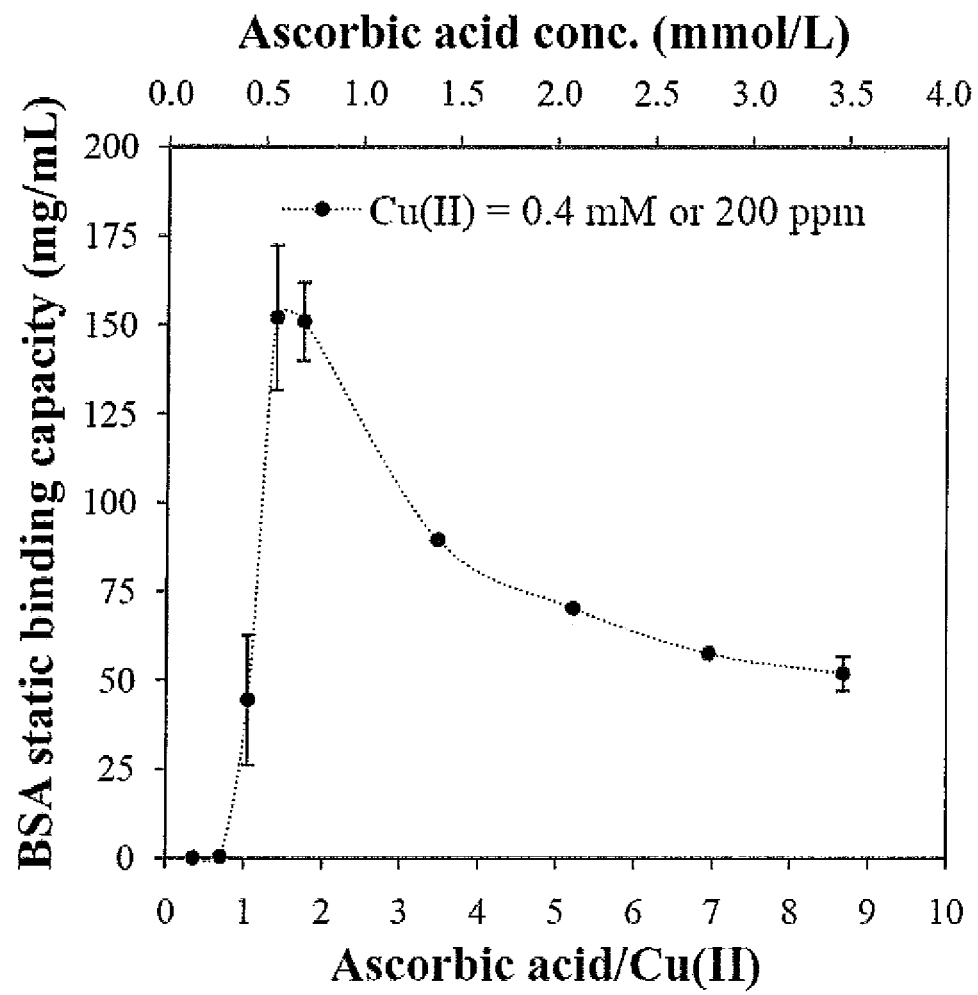
FIG. 1 represents the effect of ascorbic acid concentration during polymerization reaction on protein binding capacity of surface-modified anion-exchange membranes. The bottom x-axis represent the molar ratio of ascorbic acid to the copper (II) chloride concentration. The top x-axis represents the concentration of ascorbic acid. The y-axis represents the static protein binding capacity of bovine serum albumin (BSA) protein in milligrams per milliliter (mg/mL) of adsorptive membrane bed.

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

According to one embodiment, disclosed are methods for preparation of macroporous membranes having unusually high equilibrium protein binding capacities. Disclosed membranes can include a self-supporting porous membrane substrate and a grafted polymer film on pore surfaces of the substrate. Also disclosed are methods for grafting a polymer film on a porous membrane substrate using surface-initiated polymerization. Grafted polymer chains of a polymer film can act as molecular 'brushes' or 'tentacles' in solution and can include one or more capture chemistries, for instance one or more capture chemistries specific for biomolecules.

Membranes prepared according to disclosed methods can be used in the separation and purification of biomolecules such as proteins, nucleic acids, virus or virus-like particles, endotoxins, and the like according to adsorptive downstream bioseparation unit operations. By way of example, disclosed membranes can be utilized for membrane chromatography applications. In one embodiment, disclosed macroporous adsorptive membranes can have ion-exchange functionality produced by grafting polymeric thin films at the surface of self-supporting base porous substrates using activators regenerated by electron transfer atom transfer radical polymerization (ARGET-ATRP) or activators generated by electron transfer atom transfer radical polymerization (AGET-ATRP).

Average nominal pore size of a porous membrane substrate can range from about 0.01 micrometers (μm) to about 50 micrometers. For instance, the average nominal pore size can range from about 0.05 μm to about 15 μm, such as from about 0.10 μm to about 10 μm.

The selection of polymer for a thin film to be formed on the porous membrane substrate can be based on the pendent ion-exchange functional group available in the molecular structure of the monomer. In one embodiment, a polymeric thin film can include a homopolymer including one or more pendant ion-exchange groups provided by the monomer unit used to form the homopolymer. For instance, the monomer can be a monomer with tertiary or quaternary amine functionality. Examples of monomers that can be used include styrene, acrylate, methacrylate, acrylamide, or acrylonitrile based-monomers containing anion-exchange or cation-exchange pendant groups. For example, the monomer can be dimethylaminoethyl methacrylate (DMAEMA). The uniformity of polymer chain density and thickness of the polymeric thin film can determine the transport and adsorption properties of the resulting ion-exchange membranes.

Figure 2:
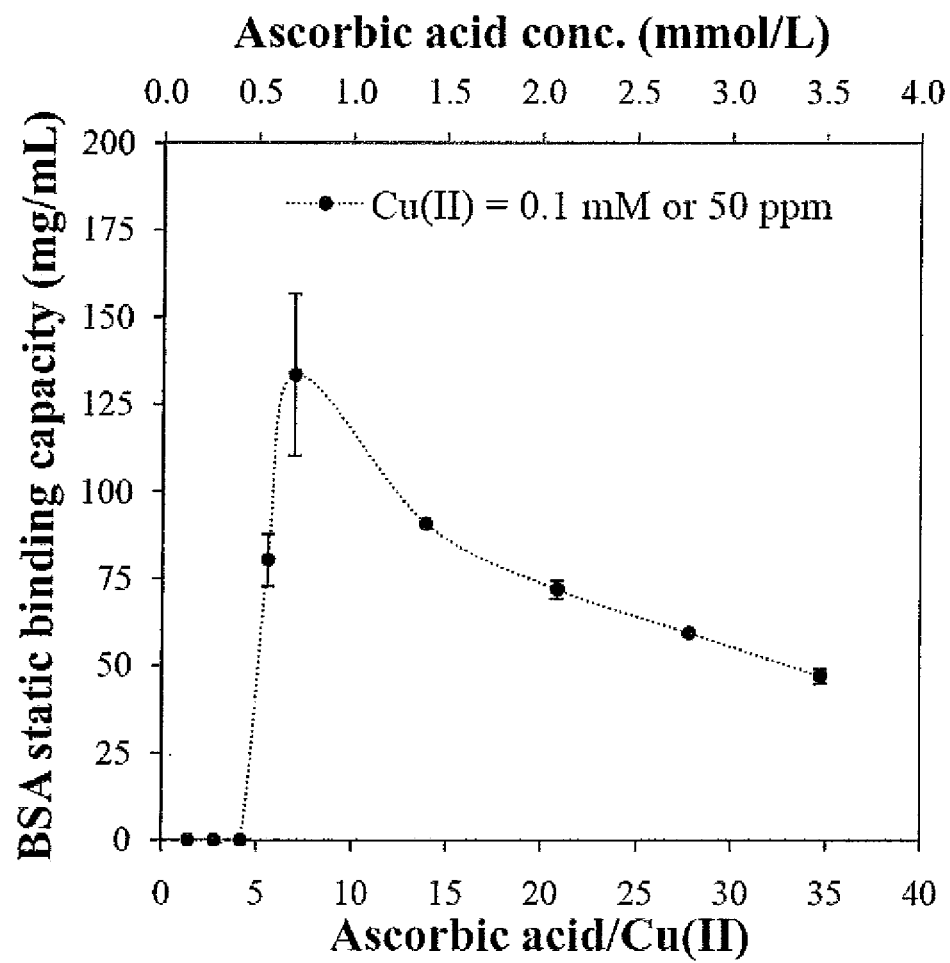
FIG. 2 represents the effect of ascorbic acid concentration during polymerization reaction on protein binding capacity of surface-modified anion-exchange membranes. The bottom x-axis represent the molar ratio of ascorbic acid to the copper (II) chloride concentration. The top x-axis represents the concentration of ascorbic acid. The y-axis represents the static protein binding capacity of BSA protein in milligrams per milliliter (mg/mL) of adsorptive membrane bed.

Regardless of the monomer used, the formation of the polymeric thin film can add mass to the porous membrane substrate. For instance, mass increase can be from about 1% to about 100% by weight of the porous membrane substrate, such as from about 1% to 50% in some embodiments and from about 1% to about 25% in still other embodiments. As shown in FIGS. 1 and 2, ion-exchange membranes prepared according to disclosed methods can have extremely high and fully reversible protein binding capacities in excess of about 150 mg/mL for proteins, such as from about 10 mg/mL to about 175 mg/mL in some embodiments and from about 25 mg/mL to about 150 mg/mL in still other embodiments. Examples of proteins that can bind to the membranes disclosed herein are bovine serum albumin and monoclonal antibodies.

According to disclosed methods, surface-initiated graft polymerization can be utilized to modify a porous membrane substrate to include a polymeric thin film. More specifically, a polymeric thin film can be prepared by a 'grafting from' approach so as to incorporate ion-exchange functionality onto the internal pore surfaces of a porous membrane substrate. More specifically, a two step surface modification process can be used to prepare the modified porous films. In the first step, membranes can be functionalized with an ATRP initiator, and in the second step, initiator-functionalized membranes can be further modified by surface-initiated ARGET or AGET-ATRP utilizing a monomer bearing ion-exchange functionality.

A typical initiator functionalization solution can include an ATRP initiator precursor and one or more solvents. Suitable ATRP initiator precursors can include organic halides such as bromine or chlorine based initiator precursors. For example, the ATRP initiator precursor can be 2-bromoisobutyryl bromide (2-BIB). Common solvents can include but are not limited to tetrahydrofuran, methanol, ethanol, acetonitrile, and mixtures of one or more of these solvents. The concentration of the ATRP initiator precursor in the solution can range from about 1 millimolar (mM) to about 40 mM, such as from about 10 mM to 30 mM in some embodiments and from about 15 mM to 20 mM in still other embodiments. The initiator functionalization can be carried out a temperature ranging from about 0° C. to about 45° C., such as at a temperature of about 35° C.

A polymerization solution for use in the second step of a process can include a monomer with ion-exchange functionality (e.g., a monomer with tertiary or quaternary amine functionality), a catalyst complex including a metal salt and ligand molecule, a solvent, and a reducing agent. Examples of monomers that can be used include styrene, acrylate, methacrylate, acrylamide, or acrylonitrile based-monomers containing anion-exchange or cation-exchange pendant groups. For example, the monomer can be dimethylaminoethyl methacrylate (DMAEMA).

Further, the metal salt can be a transition metal salt such as copper, titanium, molybdenum, rhenium, iron, ruthenium, osmium, rhodium, cobalt, nickel, or palladium. One example of a suitable metal salt is copper(II) chloride. Meanwhile, the ligand can be a nitrogen-based ligand such as an amine or the ligand can be a phosphorous ligand. For instance, the ligand can be 1,1,4,7,10,10-hexamethyltriethylenetetramine (HMTETA). Methanol, ethanol, 2-propanol, water and mixtures of one or more solvents can be used, but it should be understood that other suitable solvents can also or alternatively be used.

Ascorbic acid is one suitable reducing agent, but others can alternatively be used. For instance, other suitable reducing agents include copper oxide, tin(II) 2-ethylhexanoate, glucose, or hydrazine. In the second step, the monomer can be added to the solvent, where the concentration of the monomer in the solvent ranges from about 0.25 molar (M) to about 5 M, such as from about 0.5 M to 4 M in some embodiments and from about 1 M to 3 M in still other embodiments.

A catalyst can then be formed by the addition of the metal salt and ligand. The concentration of the metal salt in the solution can range from about 5 parts per million (ppm) to about 400 ppm, such as from about 10 ppm to about 350 ppm in some embodiments and from about 25 ppm to about 250 ppm in still other embodiments. For instance, the concentration of the metal salt in the solution can range from about 0.01 mM to about 0.8 mM, such as from about 0.02 mM to about 0.6 mM in some embodiments and from about 0.05 mM to about 0.5 mM in still other embodiments. Meanwhile, the concentration of the ligand in the solution can range from about 10 ppm to about 800 ppm, such as from about 20 ppm to about 700 ppm in some embodiments and from about 50 ppm to about 500 ppm in still other embodiments.

Next, the reducing agent can be added in an amount so that the molar ratio of reducing agent to transition metal salt can typically range from about 0 to about 100, such as from about 0 to about 40 in some embodiments, and from about 0.5 to 20 in still other embodiments. For example, the reducing agent can be added in an amount of from about 0 mM to about 8 mM, such as from about 0.25 mM to about 6 mM in some embodiments and from about 0.5 mM to 4 mM in still other embodiments.

Further, the step of modification by surface-initiated ARGET or AGET-ATRP described above can be carried out a temperature ranging from about 0° C. to about 80° C., such as at a temperature of about 40° C.

Surface-initiated ATRP, a catalyst-activated reaction, can allow independent control over polymer chain grafting density as well as the thickness of the polymeric film grafted at membrane pore surfaces. By controlling polymer chain grafting density and polymer film thickness independently, the protein binding capacity and transport properties of membranes can be optimized.

As discussed above, problems have been encountered when utilizing an ATRP process for surface modification of a membrane. Presently disclosed methods can overcome these problems by forming the active catalyst and removing dissolved oxygen simultaneously through addition of an oxygen scavenger compound to the solution.

Disclosed methods further include a polymer grafting process using surface initiated ATRP in the presence of dissolved oxygen and very low catalyst concentration to prepare surface-modified adsorptive membranes. Specifically, disclosed modified membranes can be charged adsorptive membranes.

Modified membranes formed as disclosed herein can be used in the separation and purification of charged molecules such as proteins, nucleic acids, virus or virus like particles, endotoxins, and the like. Disclosed membranes include a porous membrane substrate and a polymeric thin film grafted covalently at pore surfaces of the porous membrane substrate. In one embodiment the porous membrane substrate can be a macroporous membrane formed of a hydrophilic material. For example, the porous membrane substrate can be formed from cellulose, cellulose derivatives, regenerated cellulose or nylon. However, it is to be understood that the use of a hydrophilic material is not required, and the porous membrane substrate can be formed from other materials known to those of ordinary skill in the art, such as polysulfone, polyethersulfone, polyvinylidene fluoride, polyacrylonitrile, polyetherimide, polypropylene, polyethylene, or polyether terephthalate. A macroporous membrane substrate can exhibit high volumetric flow rate due to micron-size pores, low non-specific adsorption of proteins, and high density of surface functionality that can be used as reactive sites.

Modified membranes can be prepared using surface-initiated graft polymerization. The 'grafting from' approach, as opposed to coating or the 'grafting to' approach of other processes, realized with A(R)GET-ATRP can be used to graft polymer chains at the surface of the porous membrane substrate. A polymeric film can be made of homopolymer with ion-exchange functionality. Disclosed methods can offer independent control of thickness of polymeric film and the grafting density of polymer chains to optimize the protein binding capacity and flow properties of ion exchange membranes.

The present disclosure may be better understood with reference to the Examples, provided below.

Example 1

This example describes a method to prepare an ion-exchange membrane with an anion exchange polymeric film anchored to a porous, self-supporting, regenerated cellulose membrane matrix. Further illustrated is the protein binding capacity of the prepared membrane.

Surface modification of regenerated cellulose membranes was carried out in two steps. Initiator molecules were anchored to the membrane pore surfaces in a first step. ARGET ATRP was used in the second step to graft a thin film of poly-(2-(dimethylamino)ethyl methacrylate) (poly-(DMAEMA)) from the initiator sites. Initiator functionalization was carried out in tetrahydrofuran (THF) at 35° C. Membranes were removed from the THF and dried for 5 minutes before placing into the solution for initiation.

A typical solution comprised the initiator precursor, 2-bromoisobutyryl bromide (2-BIB) at a concentration of 18 mM, and solvent anhydrous THF (50 mL). After 2 hours (h), the membrane was removed from the reaction mixture, washed thoroughly with methanol, THF and HPLC water to remove excess unbound 2-BIB.

Initiator-functionalized membranes were modified further by surface-initiated ARGET-ATRP. A typical procedure follows: monomer, DMAEMA was added to the solvent, 2-propanol to prepare a 2 M monomer solution in a flask. A catalyst was formed by addition of copper(II) chloride (50 or 200 ppm) and amine ligand with 1,1,4,7,10,10-hexamethyltriethylenetetramine (HMTETA; 100 or 400 ppm) into the monomer solution. Next, this mixture was placed on a magnetic stir plate for 15 minutes until it became homogeneous, indicating the formation of a fully soluble catalyst complex. Initiator-functionalized membrane was placed inside a 40 mL serum glass vial and 35 mL polymerization solution was added to this vial. The glass vial was sealed using a rubber stopper and aluminum cap to make it air tight. A reducing agent, ascorbic acid (AA), was dissolved into 2-propanol solvent using a second serum glass vial. Next, this vial was placed into an ultrasonic bath for 15 minutes until ascorbic acid was solubilized. The resulting ascorbic acid solution was injected into the 40 mL serum glass vials containing the membrane and polymer solution using a syringe under air tight conditions. The temperature of the polymerization reaction mixture was raised to 40° C. by placing the glass vials in a constant temperature shaker bath. After 4 hours, the membrane was removed from the reaction mixture, washed thoroughly with methanol and HPLC water.

In the first set of experiments, the concentration of ascorbic acid was varied while the concentration of catalyst was kept constant.

The effect of ascorbic acid concentration on protein binding capacity of surface-modified ion-exchange membranes was measured using static protein binding capacity experiments.

Bovine serum albumin (BSA) was used as model protein to measure static protein adsorption capacities of modified membranes. BSA concentration of 3.0 mg/mL was prepared in 10 mM PBS buffer. Each membrane (47 mm diameter) was placed in a 40 mL glass bottle (IChem*short, wide-mouth, Fisher Scientific) and incubated in 10 mL protein solution for 20 hours to reach equilibrium in a shaker bath at 22° C. Next, membranes were removed from the glass bottles and equilibrium concentrations of the protein solutions were measured. Binding capacities, reported as the adsorbed mass of protein per unit volume of membrane, were calculated by mass balance using initial and equilibrium concentrations of protein solution determined from a calibration plot.

As shown in FIG. 1, when the concentration of copper(II) chloride is about 0.4 mM or 200 µm, the BSA static binding capacity ranges from about 0 mg/mL to about 150 mg/mL. For example, to achieve a BSA static binding capacity of from about 125 mg/mL to about 150 mg/mL, the absorbic acid concentration ranges from about 0.4 to about 1 mM, resulting in a ratio of absorbic acid to copper(II) chloride that is between 1 and 2.5.

Example 2

This example describes a method to prepare an ion-exchange membrane with an anion exchange polymeric film anchored to a porous, self-supporting, regenerated cellulose membrane matrix. Further illustrated is the protein binding capacity of the prepared membrane. The experimental method described in EXAMPLE 1 was used to prepare membranes. In this set of experiments, the concentration of catalyst was reduced four-fold, while the molar ratio of ascorbic acid to catalyst was kept constant. The effect of catalyst concentration on protein binding capacity of surface-modified ion-exchange membranes was measured using static protein binding capacity experiments.

As shown in FIG. 2, when the concentration of copper(II) chloride is reduced four-fold to about 0.1 mM or 50 ppm, the BSA static binding capacity ranges from about 0 mg/mL to about 150 mg/mL, even though the ratio of absorbic acid reducing agent to copper(II) chloride is larger than in EXAMPLE 1 due the reduction in the concentration of copper(II) chloride used. For example, to achieve a BSA static binding capacity of from about 125 mg/mL to about 150 mg/mL using only 0.1 mM copper(II) chloride, the absorbic acid concentration is still from about 0.4 to 1 mM, resulting in a ratio of absorbic acid to copper(II) chloride that is between 4 and 10.

Example 3

Figure 3:
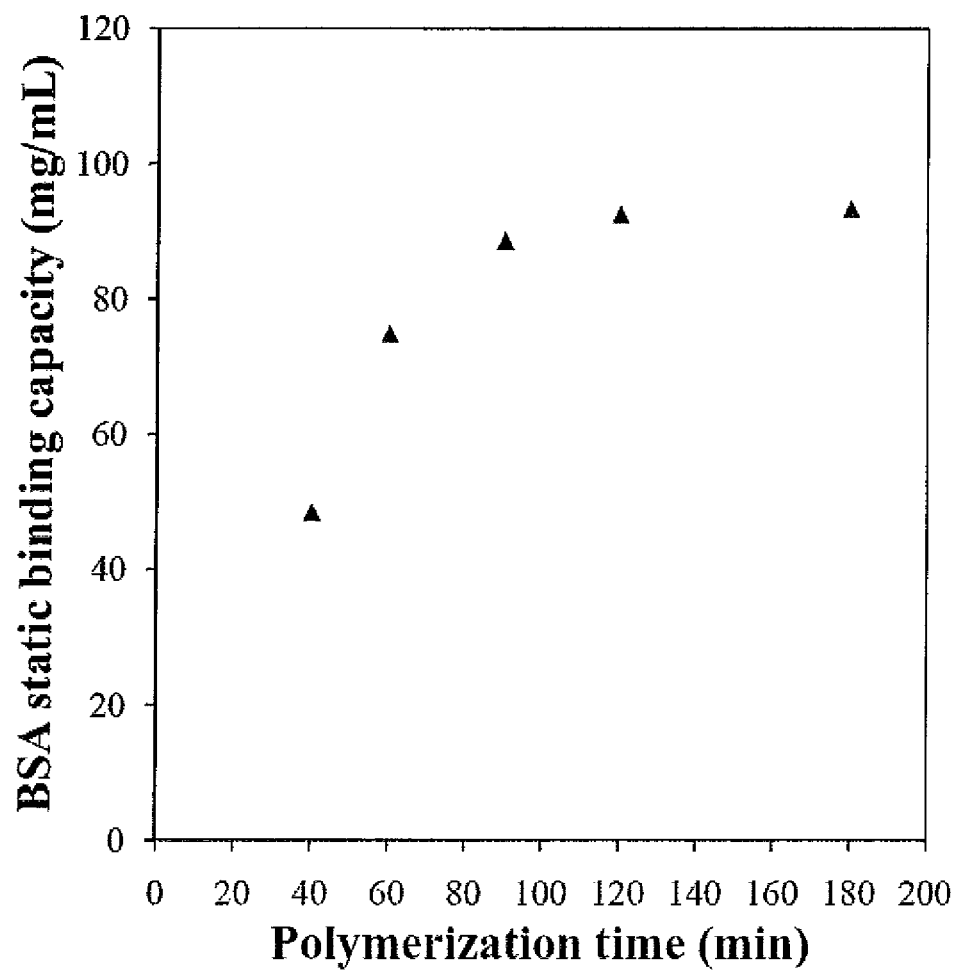
FIG. 3 represents the effect of polymerization reaction time on protein binding capacity of surface-modified anion-exchange membranes. The bottom x-axis represent the polymerization time in minutes. The y-axis represents the static protein binding capacity of BSA protein in milligrams per milliliter (mg/mL) of adsorptive membrane bed.

This example describes a method to prepare an ion-exchange membrane with an anion exchange polymeric film anchored to a porous, self-supporting, regenerated cellulose membrane matrix. Further illustrated is the protein binding capacity of the prepared membrane. The experimental method described in EXAMPLE 1 was used to prepare membranes. In this set of experiments, the polymerization time, thus, the degree of polymer grafting, was varied at constant concentrations of catalyst and ascorbic acid. The effect of polymerization time on protein binding capacity of surface-modified ion-exchange membranes was measured using static protein binding capacity experiments. As shown in FIG. 3, the BSA static binding capacity reached its maximum value at a polymerization time of from about 120 minutes to about 200 minutes.

While certain embodiments of the disclosed subject matter have been described using specific terms, such description is for illustrative purposes only, and it is to be understood that changes and variations may be made without departing from the spirit or scope of the subject matter.

What is claimed is:

1. A method of forming an ion-exchange membrane, comprising:
   providing a porous substrate having pore surfaces, wherein the substrate is self-supporting;
   anchoring initiator molecules to the pore surfaces by immersing the substrate into an initiator functionalization solution to form initiator sites on the substrate; and
   grafting a polymer film from the initiator sites via surface-initiated activators regenerated by electron transfer-atom transfer radical polymerization (ARGET-ATRP) or activators generated by electron transfer-atom transfer radical polymerization (AGET-ATRP) by immersing the substrate into a polymerization solution and adding a reducing agent to the solution, wherein the membrane has a protein binding capacity in excess of about 100 milligrams per milliliter.

2. The method according to claim 1, wherein the porous substrate has an average nominal pore size of from about 0.05 micrometers to about 15 micrometers.

3. The method according to claim 1, wherein the porous substrate comprises cellulose, a cellulose derivative, regenerated cellulose, nylon, polysulfone, polyethersulfone, polyvinylidene fluoride, polyacrylonitrile, polyetherimide, polypropylene, polyethylene, or polyether terephthalate.

4. The method according to claim 1, wherein the initiator functionalization solution comprises an atom transfer radical polymerization (ATRP) initiator precursor and one or more solvents.

5. The method according to claim 4 where the ATRP initiator precursor comprises an organic halide.

6. The method according to claim 5 wherein the ATRP initiator precursor comprises 2-bromoisobutyryl bromide.

7. The method according to claim 4, wherein the one or more solvents comprises tetrahydrofuran, methanol, acetonitrile, or combinations thereof.

8. The method according to claim 1, wherein the anchoring is carried out at a temperature of from about 0° C. to about 45° C.

9. The method according to claim 1, wherein the polymerization solution comprises a solvent, one or more monomers, and a catalyst complex, wherein the catalyst complex comprises a transition metal salt and a ligand, wherein the ligand is an amine ligand or a phosphorous ligand.

10. The method according to claim 9, wherein the one or more monomers has ion-exchange functionality, and further wherein the one or more monomers comprises styrene, acrylate, methacrylate, acrylamide, or acrylonitrile.

11. The method according to claim 10, wherein the polymer comprises dimethylaminoethyl methacrylate (DMAEMA).

12. The method according to claim 9, wherein the transition metal salt comprises copper(II) chloride and the amine ligand comprises 1,1,4,7,10,10-hexamethyltriethylenetetramine (HMTETA).

13. The method according to claim 12, wherein the molar concentration of the copper(II) chloride in the polymerization solution is from about 0.01 millimolar to about 0.8 millimolar.

14. The method according to claim 9, wherein the ratio of the reducing agent to the transition metal salt ranges from about 0.5 to about 20.

15. The method according to claim 1, wherein the reducing agent comprises ascorbic acid.

16. The method according to claim 15, wherein the molar concentration of the ascorbic acid in the polymerization solution is from about 0.25 millimolar to about 5 millimolar.

17. The method according to claim 1, wherein the grafting is carried out at a temperature of from about 0° C. to about 80° C.

18. An ion-exchange membrane, comprising:
   a porous substrate, wherein the substrate comprises pore surfaces and is self-supporting;
   initiator sites at the pores surfaces, wherein the initiator sites are formed by immersing the substrate into an initiator functionalization solution; and
   a polymer film grafted from the initiator sites via surface-initiated activators regenerated by electron transfer-atom transfer radical polymerization (ARGET-ATRP) or activators generated by electron transfer-atom transfer radical polymerization (AGET-ATRP), wherein the membrane has a protein binding capacity in excess of about 100 milligrams per milliliter.

19. The membrane according to claim 18, wherein the porous substrate has an average nominal pore size of from about 0.05 micrometers to about 15 micrometers.

20. The membrane according to claim 18, wherein the porous substrate comprises cellulose, a cellulose derivative, regenerated cellulose, nylon, polysulfone, polyethersulfone, polyvinylidene fluoride, polyacrylonitrile, polyetherimide, polypropylene, polyethylene, or polyether terephthalate.

21. The membrane according to claim 18, wherein the initiator sites comprise an ATRP initiator precursor.

22. The membrane according to claim 21, wherein the ATRP initiator precursor comprises an organic halide.

23. The membrane according to claim 3, wherein the organic halide comprises 2-bromoisobutyryl bromide.

24. The membrane according to claim 18, wherein the polymer film comprises one or more monomers with ion-exchange functionality, wherein the one or more monomers comprises styrene, acrylate, methacrylate, acrylamide, or acrylonitrile.

25. The membrane according to claim 24, wherein the polymer film comprises dimethylaminoethyl methacrylate (DMAEMA).

26. The membrane according to claim 18, wherein the membrane is used in the separation and purification of biomolecules including proteins, nucleic acids, viruses, virus-like particles, and endotoxins.

\* \* \* \* \*